US00PP08192P

United States Patent [19]

Holden

[11] Patent Number: Plant 8,192

[45] Date of Patent: Mar. 30, 1993

[54] VARIETY OF GERANIUM NAMED ELIZABETH

[75] Inventor: Douglas Holden, Solvang, Calif.

[73] Assignee: Bodger Seeds, Ltd., So. El Monte, Calif.

[21] Appl. No.: 830,235

[22] Filed: Jan. 31, 1992

[51] Int. Cl.[5] ..... A01H 5/00

[52] U.S. Cl. ..... Plt./87.12

[58] Field of Search ..... Plt./87.12

*Primary Examiner*—James R. Feyrer

*Attorney, Agent, or Firm*—Webb, Burden, Ziesenheim & Webb

[57] ABSTRACT

The cultivar is characterized by its bright orange-red color. Its compact, controlled growth habit and prolific blooms provide for superb cuttings and performs equally well in a hanging basket as well as in a ground bed. The blooms hold up well in high summer temperatures and produce quickly after rain.

1 Drawing Sheet

BACKGROUND OF THE INVENTION

The present invention comprises a new and distinct cultivar of *Pelargonium*×*hortorum* known by the varietal name Elizabeth (Oglevee No. 7068; Bodger No. 200-1). The new variety was discovered in a selected breeding program at Bodger Seeds, Ltd. in Lompoc, Calif. in November, 1987. The new variety is a selection from the crossing of (Salmon Floral Cascade×Pinto Red)×Red Elite. The new variety was first asexually reproduced by cuttings at Bodger Seeds, Ltd. on Jan. 25, 1988. The new variety has been asexually reproduced by cuttings at Oglevee Ltd. in Connellsville, Penna. over a three year period. It has also been trial and field tested at Connellsville and has been found to retain its distinctive characteristics through successive propagations.

The cultivar when grown in a glass greenhouse in Connellsville, Penna. using natural light and 60° F. night, 68° F. day and 71° F. vent, has a response time of six weeks from a rooted cutting to flowering in a 10 cm pot. The response time was determined on plants grown in soilless media employing constant fertilizer of 200 parts per million of nitrogen and potassium in full light. The rooted cuttings were potted on Feb. 19, 1991 and flowered on Apr. 2, 1991.

DESCRIPTION OF THE DRAWING

FIG. 1 of the accompanying photographic drawing illustrates the new cultivar the color being as nearly true as possible with color illustrations of this type.

DESCRIPTION OF THE NEW PLANT

The following detailed description sets forth the characteristics of the new cultivar. The data which defines these characteristics were collected by asexual reproductions carried out by Oglevee Ltd. in Connellsville, Penna. The plant history was taken on six week plants blossomed under natural light in a greenhouse and the color readings were taken indoors under 200–220 foot candles of florescent cool white light. Color references are primarily to The R.H.S Color Chart of The Royal Horticultural Society of London.

THE PLANT

Classification:

*Botanical.*—*Pelargonium*×*hortorum.*

*Commercial.*—Zonal Geranium.

Form: Uniform mound, free basal branching, compact.

*Height.*—16–17 cm from media surface.

*Growth.*—Self-branching, mound-like habit with some cascading growth.

Strength: This plant performs equally well in a hanging basket or in a ground bed.

Foliage: Distinct zone present; stalked leaf attachment.

Leaves:

*Size.*—6.5–7.0 cm across.

*Shape.*—Reniform; cordate base.

*Margin.*—Crenate.

*Texture.*—Lightly pubescent, slightly reflective.

*Color.*—Top: Green Group 137B. Zone: Greyed-Purple Group 183A. Bottom: Yellow-Green Group 147B.

*Ribs and veins.*—Palmate venation. Color: Yellow-Green Group 146D.

Petioles:

*Color.*—Yellow-Green Group 146C.

*Length.*—6.5–8.5 cm in length.

Stem:

*Color.*—Yellow-Green Group 146D.

*Internodes.*—1.0–2.5 cm in length.

THE BUD

Shape: Upright; hemispherical cluster.

Size: 1.0–2.0 cm across.

INFLORESCENCE

Blooming habit: Continuous; upright, floriferous blooming.

Size: 6.5–7.5 cm across.

Borne: Florets on pedicel, pedicel on peduncle; 4.5–6.0 cm above foliage.

Florets:

*Form.*—Flat to slightly cupped.

*Color.*—Top: Red Group 43A. Bottom: Red Group 41B.

*Petals.*—6–11 in number, obovate; margin entire; separate, not united; flat to slightly cupped.

*Size.*—0.5–1.5 cm across at the widest point, 1.0–1.5 cm in length.

*Texture and appearance.*—Smooth; from a distance bloom appears a bright orange-red above foliage of medium green with a dark zone.

Petaloids:

*Quantity.*—4–6 in number.

*Shape.*—Narrow, elongated, twisted, some tubular.

*Color.*—Red Group 43A.

Pedicel:

*Length.*—2.5–3.0 cm in length.

*Color.*—Yellow-Green Group 146B with a cast of Greyed-Red Group 182A on the floret end of the pedicel.

Peduncle: Arises from the nose opposite the leaf petiole; 16.0–16.5 cm in length.

*Color.*—Yellow-Green Group 146B.

Disease resistance: Not known.

Lasting quality: Holds up well in high summer temperatures and has the ability to produce new blooms quickly after rain.

REPRODUCTIVE ORGANS

Stamens:

*Anthers.*—2 mm in length.

*Filaments.*—6–8 mm in length.

*Pollen.*—Golden brown.

Pistils:

*Number.*—One.

*Length.*—8 mm.

*Stigma.*—5–6 parted, red-purple in color.

*Style.*—3 mm.

Ovaries: Pubescent; pale green in color; superior; 4–5 mm in length, 2 mm across.

Fruit: None present.

GENERAL CHARACTERISTICS

This new Geranium variety, Elizabeth, is an improvement over the current Floribunda Brigette. It is an improvement over Brigette as a result of its clearer orange-red color inherited from Red Pinto and Red Elite, as well as a more compact and controlled growth habit.

The plant still performs extremely well outdoors in either a hanging basket or in ground beds. Elizabeth blooms very prolifically, provides a compact, full-growth habit similar to that of Salmon Floral Cascade and is still a superb cutting producer. It has good lasting quality and the ability to bloom quickly after a rain.

The dark zone on the medium green foliage and the bright orange-red flowers create an eye appealing novelty for the home gardener.

I claim:

1. A new and distinct variety of Geranium plant, substantially as shown and described.

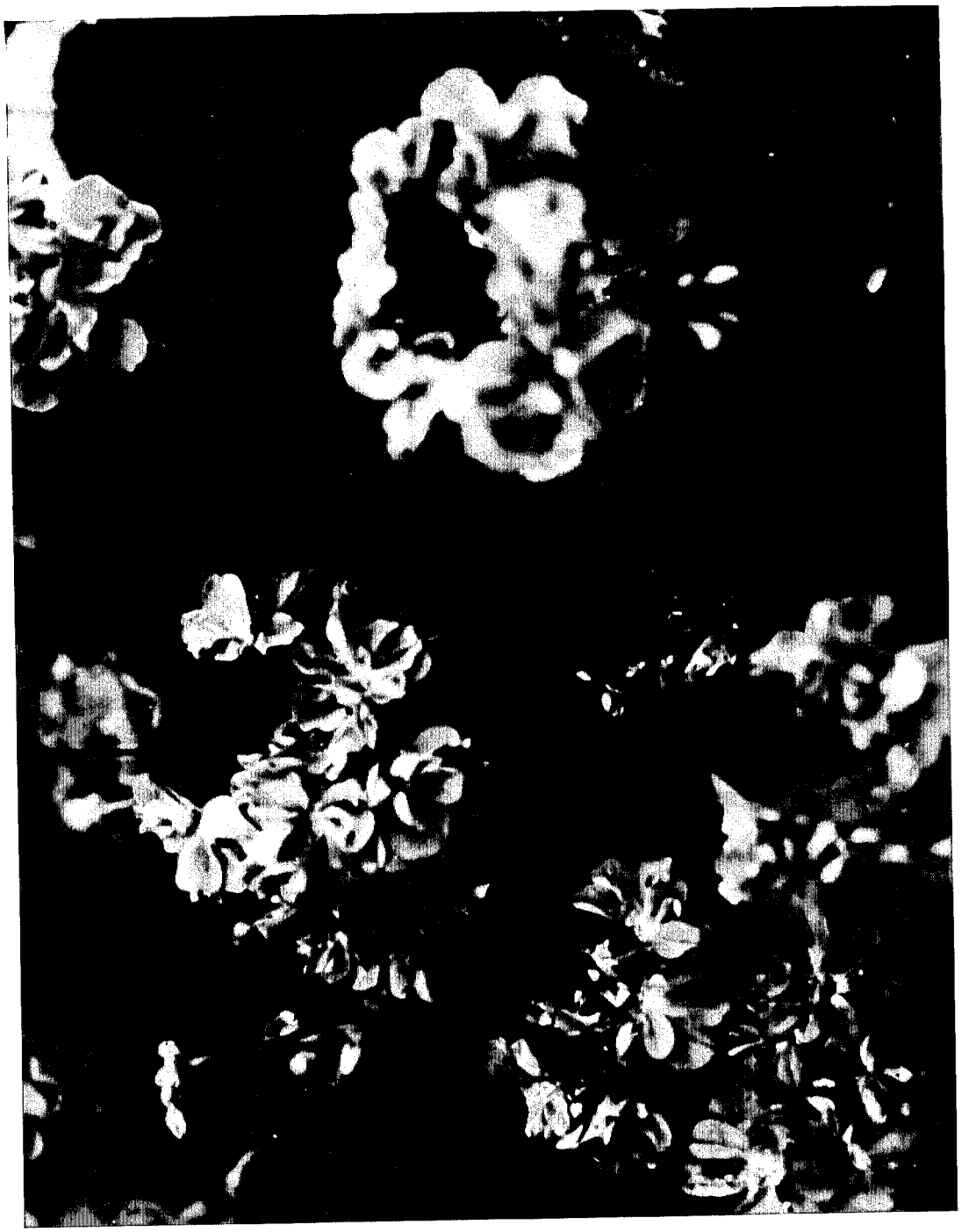

* * * * *